United States Patent
Nishiyama

(10) Patent No.: US 6,766,696 B2
(45) Date of Patent: Jul. 27, 2004

(54) COATING ADHESION STRENGTH AND SHEAR STRENGTH MEASURING APPARATUS

(75) Inventor: Ituo Nishiyama, Itami (JP)

(73) Assignee: Daipla Wintes Co., Ltd., Saitama (JP)

( * ) Notice: Subject to any disclaimer, the term of this patent is extended or adjusted under 35 U.S.C. 154(b) by 0 days.

(21) Appl. No.: 10/370,981

(22) Filed: Feb. 20, 2003

(65) Prior Publication Data

US 2003/0172749 A1 Sep. 18, 2003

(30) Foreign Application Priority Data

Mar. 13, 2002 (JP) ........................................ 2002-068820

(51) Int. Cl.$^7$ ............................................. G01B 21/32
(52) U.S. Cl. ...................................................... 73/762
(58) Field of Search ........................ 73/762, 827, 104, 73/150 A, 159, 845; 83/34; 144/211

(56) References Cited

U.S. PATENT DOCUMENTS

| | | | | |
|---|---|---|---|---|
| 4,934,185 A | | 6/1990 | Nishiyama et al. | |
| 5,111,688 A | * | 5/1992 | Houghton et al. | 73/159 |
| 5,333,494 A | * | 8/1994 | Kishima et al. | 73/104 |
| 5,483,729 A | * | 1/1996 | Fayard | 26/15 R |

* cited by examiner

Primary Examiner—Edward Lefkowitz
Assistant Examiner—Octavia Davis
(74) Attorney, Agent, or Firm—Jordan and Hamburg LLP

(57) ABSTRACT

Coating adhesive strength and shear strength measuring apparatus for measuring adhesive strength and shear strength of a coating of a test piece including a vertical pressure sensor linked at one end to a guide shaft which is movable in vertical and parallel directions relative to the coating surface of the test piece while a parallel pressure sensor is linked at its first end by a link to the other end of the vertical pressure sensor. The second end of the parallel pressure sensor is linked to a cutting knife. As the coating of the test piece is sliced with the cutting knife, the vertical pressure and the parallel pressure exerted on the cutting knife can be measured.

18 Claims, 3 Drawing Sheets

(Fig. 1)
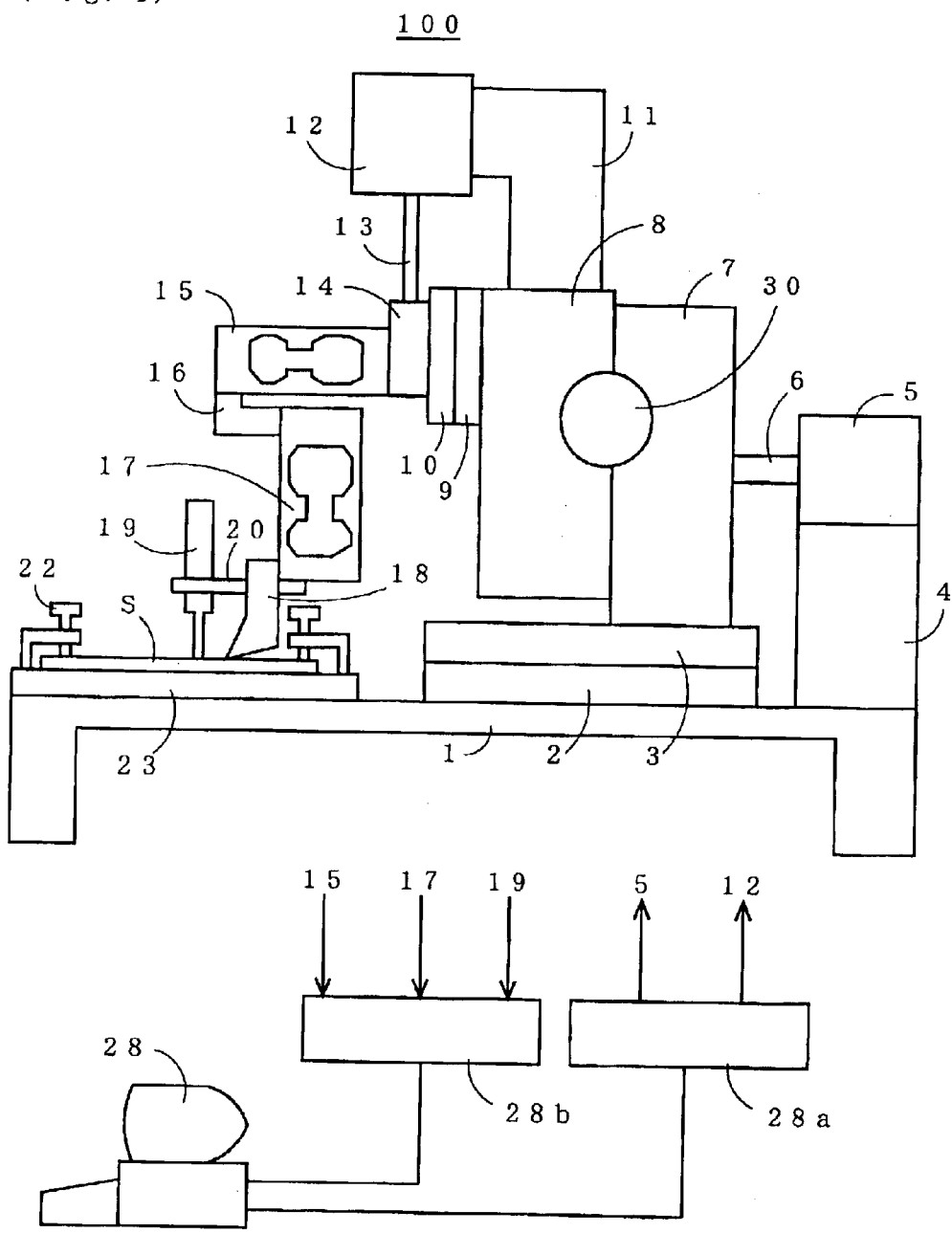

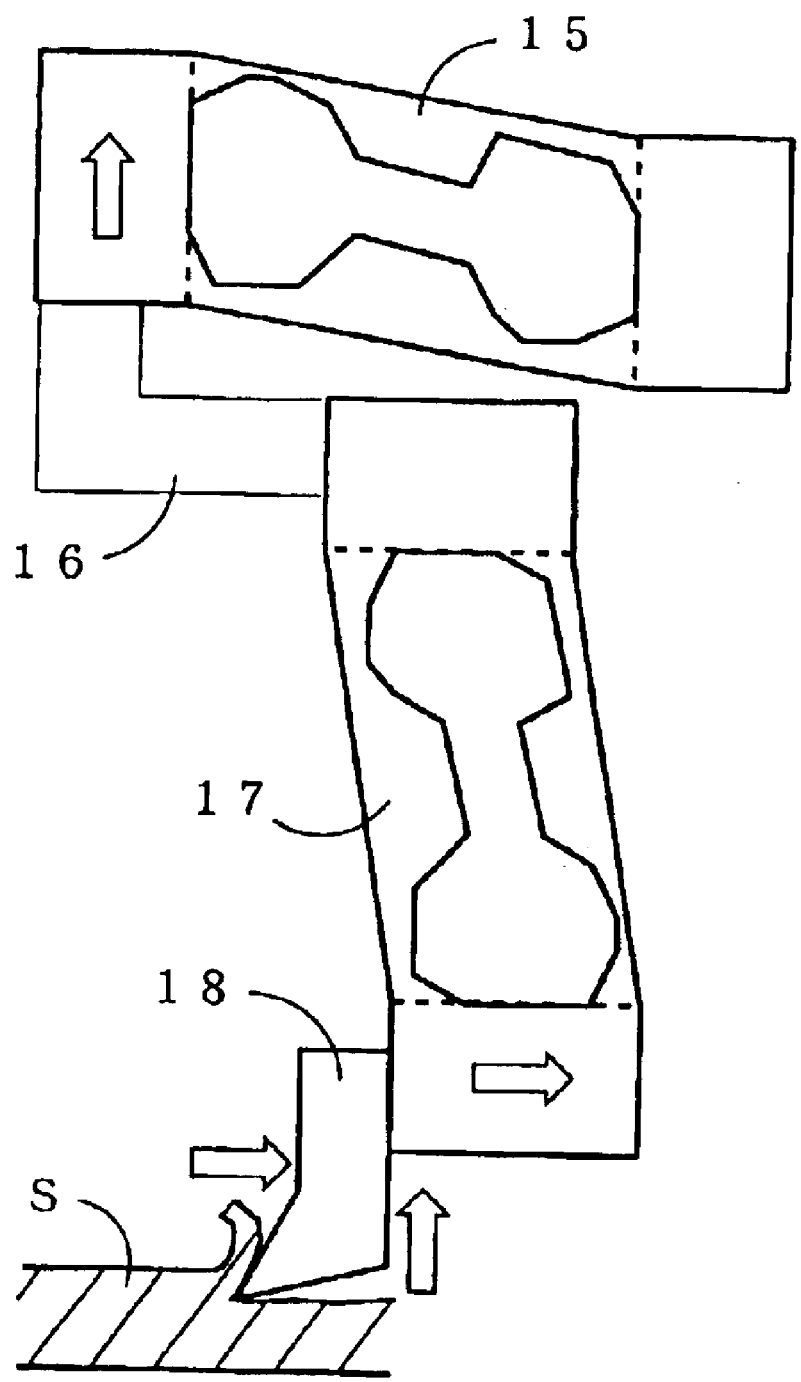
(Fig. 2

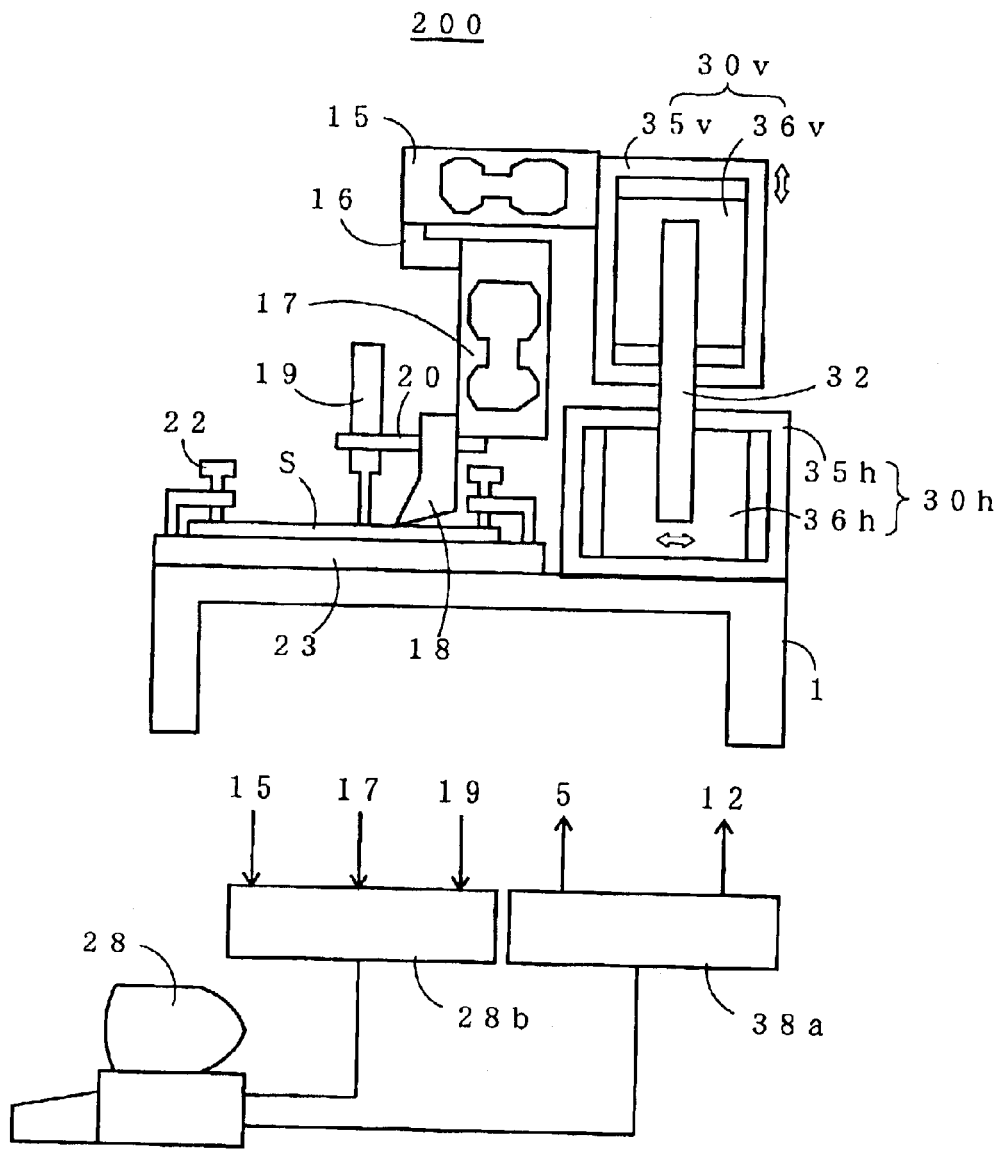
(Fig. 3)

COATING ADHESION STRENGTH AND SHEAR STRENGTH MEASURING APPARATUS

BACKGROUND OF THE INVENTION

1. Field of the Invention

The present invention relates to a coating adhesive strength and shear strength measuring apparatus and more particularly to a coating adhesive strength and shear strength measuring apparatus which can accurately measure the adhesive strength and the shear strength of a coating film bonded to a test piece while its structure is simple and low in the cost.

2. Description of the Related Art

Disclosed in Japanese Patent Laid-open Publication (Heisei)3-67151 is a conventional coating adhesive strength and shear strength measuring apparatus which comprises a cutting knife holder arranged for moving in two, vertical and parallel, directions relative to a vertical sliding guide shaft which can be moved in vertical to the coating surface of a test piece and a parallel sliding guide shaft which can be moved in parallel to the coating surface, a cutting knife mounted to the cutting guide shaft for slicing the coating, a vertical pressure sensor for measuring a repulsion in the vertical direction along the vertical sliding guide shaft, and a parallel pressure sensor for measuring a resistance to the cutting action in the parallel direction along the parallel sliding guide shaft.

The conventional coating adhesive strength and shear strength measuring apparatus is designed for measuring the repulsion in the vertical direction from a displacement of the vertical sliding guide shaft and the resistance to the cutting action in the parallel direction from a displacement of the parallel sliding guide shaft. Accordingly, a measurement of the repulsion includes a sliding related resistance derived from the displacement of the vertical sliding guide shaft while a measurement of the resistance to the cutting action includes a sliding related resistance derived from the displacement of the parallel sliding guide shaft.

It is however disadvantageous that the measurements of the repulsion and the resistance to the cutting action are substantially incorrect as they include the sliding related resistance on the sliding guide shafts.

Also, since there is a play gap (clearance) between the vertical sliding guide shaft and its supporting members, the depth of the cutting may be incorrect. Equally, as a play gap (clearance) is provided between the parallel sliding guide shaft and its supporting members, the cutting plane may hardly be smooth. Accordingly, the cutting plane will be elongated with much difficulty.

Moreover, the arrangement including both the vertical sliding guide shaft and the parallel sliding guide shaft becomes intricate and its overall cost win be increased.

It is hence an object of the present invention to provide a coating adhesive strength and shear strength measuring apparatus which can accurately measure the adhesive strength and the shear strength of the coating of a test piece while being simple in the structure and inexpensive in the cost.

SUMMARY OF THE INVENTION

As a first feature of the present invention, a coating adhesive strength and shear strength measuring apparatus for cutting the coating of a test piece with a cutting knife, measuring the force vertical to the coating and the force parallel to the coating which both are exerted on the cutting knife, and calculating the adhesive strength and the shear strength of the coating is provided comprising: a stage means arranged movable in two, vertical and parallel, directions relative to the coating; a vertical pressure sensor linked at one end to the stage means; a parallel pressure sensor linked at its first end to the other end of the vertical pressure sensor; and the cutting knife linked to the second end of the parallel pressure sensor, wherein the vertical force exerted on the cutting knife is measured by the vertical pressure sensor and the parallel force exerted on the cutting knife is measured by the parallel pressure sensor.

In action, the stage means may be moved while the test piece remains stationary. Alternatively, the test piece may be moved while the stage means remains stationary or both may be moved.

The coating adhesive strength and shear strength measuring apparatus of the first feature has the cutting knife mounted to the parallel pressure sensor with no sliding guide shaft disposed between the cutting knife and the parallel pressure sensor. This allows the parallel pressure to suffer from no sliding related resistance and its measurement to be accurate. Also, the cutting knife is linked by the parallel pressure sensor to the vertical pressure sensor with no sliding guide shaft disposed between the cutting knife and the vertical pressure sensor. This allows the vertical pressure to suffer from no sliding related resistance and its measurement to be accurate. Moreover, the cutting depth and the cutting plane can be affected by no sliding guide shaft play. Accordingly, both the adhesive strength and the shear strength of the coating of a test piece can be measured at higher accuracy. As no sliding guide shaft is involved, the structure of the apparatus will be simple and inexpensive.

As a second feature of the present invention, a coating adhesive strength and shear strength measuring apparatus for cutting the coating of a test piece with a cutting knife, measuring the force vertical to the coating and the force parallel to the coating which both are exerted on the cutting knife, and calculating the adhesive strength and the shear strength of the coating is provided comprising: a stage means arranged movable in two, vertical and parallel, directions relative to the coating; a parallel pressure sensor linked at one end to the stage means; a vertical pressure sensor linked at its first end to the other end of the parallel pressure sensor; and the cutting knife linked to the second end of the vertical pressure sensor, wherein the vertical force exerted on the cutting knife is measured by the vertical pressure sensor and the parallel force exerted on the cutting knife is measured by the parallel pressure sensor.

In action, the stage means may be moved while the test piece remains stationary. Alternatively, the test piece may be moved while the stage means remains stationary or both may be moved.

The coating adhesive strength and shear strength measuring apparatus of the second feature has the cutting knife mounted to the vertical pressure sensor with no sliding guide shaft disposed between the cutting knife and the vertical pressure sensor. This allows the vertical pressure to suffer from no sliding related resistance and thus its measurement to be accurate. Also, the cutting knife is linked by the vertical pressure sensor to the parallel pressure sensor with no sliding guide shaft disposed between the cutting knife and the parallel pressure sensor. This allows the parallel pressure to suffer from no sliding related resistance and thus its measurement to be accurate. Moreover, the cutting depth and the cutting plane can be affected by no sliding guide shaft play. Accordingly, both the adhesive strength and the shear strength of the coating of a test piece can be measured at higher accuracy. As no sliding guide shaft is involved, the structure of the apparatus will be simple and inexpensive.

As a third feature of the present invention, the coating adhesive strength and shear strength measuring apparatus is modified wherein the stage means is slightly moved up to 500 μm by the action of piezoelectric devices.

The stage means may be implemented by an XY stage driven by a stepping motor or an ultrasonic oscillating motor. As the XY stage has sliding portions, its clearance should allow a margin of 1 μm. The clearance may however produce an error in the measurement.

The coating adhesive strength and shear strength measuring apparatus of the third feature has the movable stage driven by piezoelectric devices and its overall components including the support base and the cutting knife can thus assembled integrally with no involvement of clearance. Accordingly, the measurement can be improved in the accuracy.

As a fourth feature of the present invention, the coating adhesive strength and shear strength measuring apparatus further comprises a graphic means for converting changes in the vertical pressure measured by the vertical pressure sensor, the parallel pressure measured by the parallel pressure sensor, and the depth of cutting by the cutting knife into graphic representations.

The coating adhesive strength and shear strength measuring apparatus of the fourth feature allows changes in the vertical pressure, the parallel pressure, and the cutting depth measured to be converted into graphic representations which can explicitly exhibit the relationship between the changes.

BRIEF DESCRIPTION OF THE DRAWINGS

FIG. 1 is a front explanatory view of the structure of a coating adhesive strength and shear strength measuring apparatus according to a first embodiment of the present invention;

FIG. 2 is a primary explanatory view illustrating a cutting action on the coating of the coating adhesive strength and shear strength measuring apparatus of the embodiment of the present invention; and FIG. 3 is a front explanatory view of the structure of a coating adhesive strength and shear strength measuring apparatus according to a second embodiment of the present invention.

DETAILED DESCRIPTION OF THE PREFERRED EMBODIMENTS

Some embodiments of the present invention will be described referring to the relevant drawings. It would be understood that the present invention is not limited to the embodiments.

(First Embodiment)

FIG. 1 is a front explanatory view of a coating adhesive strength and shear strength measuring apparatus showing the first embodiment.

The coating adhesive strength and shear strength measuring apparatus denoted at 100 has a guide shaft 2 fixedly mounted on a support bed 1. A sliding member 3 is movably mounted on the guide shaft 2.

A nut unit 7 has a threaded rod 6 screwed therein and is fixedly mounted to the sliding member 3.

The threaded rod 6 is joined at the other end to a parallel motion motor 5. As the parallel motion motor 5 rotates, the threaded rod 6 is spun to actuate the sliding movement in a horizontal direction of the nut unit 7.

The parallel motion motor 5 is a stepping motor fixedly mounted to a stationary block 4.

A pivotal head 8 is joined to the nut unit 7 and arranged for pivotal movement on the vertical plane with the use of a knob 30.

The pivotal head 8 may be replaced by a tiltable test piece head.

A guide shaft 9 has a sliding member 10 movably mounted thereon and is fixedly mounted to the pivotal head 8.

A nut unit 14 has a threaded rod 13 threaded therein and is fixedly mounted to the sliding member 10.

The threaded rod 13 is joined at the other end to a vertical motion motor 12. As the vertical motion motor 12 rotates, the threaded rod 13 is spun to actuate the sliding movement in a vertical direction of the nut unit 14.

The vertical motion motor 12 is a stepping motor fixedly mounted by a link 11 to a stationary block 8.

A vertical pressure sensor 15 is fixedly mounted at one end to the nut unit 14.

The vertical pressure sensor 15 is a weighing load cell (e.g. the trade name "CB17" of MINEBEA Co.,Ltd) for measuring the pressure exerted in a vertical direction on the other end thereof.

The first end of a parallel pressure sensor 17 is fixedly mounted by a link 16 to the other end of the vertical pressure sensor 15.

The parallel pressure sensor 17 is a weighing load cell (e.g. CB17 of MINEBEA CO.,LTD) for measuring the pressure exerted in a horizontal direction on the second end thereof.

A cutting knife 18 is fixedly mounted to the second end of the parallel pressure sensor 17.

In addition, a vertical displacement sensor 19 is fixedly mounted by a support 20 to a cutting knife holder end of the parallel pressure sensor 17.

A test piece S is a coated strip which is held with its coating surface extending horizontally between a test piece bed 23 and a clamp 22.

The parallel motion motor 5 and the vertical motion motor 12 are electrically connected by an output interface 28a to a personal computer 28.

The vertical pressure sensor 15, the parallel pressure sensor 17, and the vertical displacement sensor 19 are connected by an input interface 28b to the personal computer 28.

Upon receiving a command from the operator, the personal computer 28 actuates both the parallel motion motor 5 and the vertical motion motor 12 to cut the coating of the test piece S. The personal computer 28 then receives a measurement of the vertical pressure from the vertical pressure sensor 15, a measurement of the parallel pressure from the parallel pressure sensor 17, and a depth of the cutting from the vertical displacement sensor 19. The vertical pressure, the parallel pressure, and the depth of the cutting are then converted into graphic representations which are displayed on a display or printed down by a printer.

The measurement of the coating adhesive strength and shear strength is conducted by the following steps.

(1) A test piece S is placed on the test piece bed 23 by the clamp 22 with its coating surface extending horizontally. The edge of the cutting knife 18 is set in parallel to the coating surface of the test piece S. In case of using a tiltable test piece head, the coating surface of the test piece S is set in parallel to the edge of the cutting knife 18.

(2) The cutting knife 18 is lifted down by the action of the vertical motion motor 12 until it exerts a predetermined load (e.g. 1 g) against the coating surface of the test piece S. It is then determined that the depth of the cutting read from the vertical displacement sensor 19 is zero at the time.

(3) The cutting knife 18 is needed in both, horizontal and vertical, directions by the action of the parallel motion motor 5 and the vertical motion motor 12 so that its edge cuts into the coating of the test piece S as shown in FIG. 2. In case that the two pressure sensors 15 and 17 are forced and deformed by any pressure during the cutting operation, the cutting plane is constantly kept parallel due to maintain the shape of parallelogram thus holding the cutting knife 18 at a desired cutting angle to the test piece S.

(4) The vertical pressure (a repulsion) is measured from the output of the vertical pressure sensor 15, the parallel pressure (a resistance to the cutting action) is measure from the output the parallel pressure sensor 17, and the depth of the cutting is measured from the output of the vertical displacement sensor 19. The measurements of the changes in the vertical pressure, parallel pressure, and depth of the cutting are then examined.

Although the vertical pressure possibly affects the measurement of the parallel pressure of the parallel pressure sensor 17, it is much smaller than the parallel pressure in common practice and may be negligible. Also, the parallel pressure may affect the measurement of the vertical pressure of the vertical pressure sensor 15. This can be avoided by calculating the affection of the parallel pressure over the measurement in advance and eliminating it with its offset value. Alternatively, any affection can be ignored when the measurement is examined in its relative value but not absolute value.

The coating adhesive strength and shear strength measuring apparatus 100 of this embodiment provides the following advantages.

(1) As no sliding guide shaft is provided between the cutting knife 18 and the parallel pressure sensor 17, the apparatus is free from any sliding resistance and can thus measure the parallel pressure at higher accuracy. Similarly, as no sliding guide shaft is provided between the cutting knife 18 and the vertical pressure sensor 15, the apparatus is free from any sliding resistance and can thus measure the vertical pressure at higher accuracy.

(2) The cutting depth and the cutting plane can be affected by no sliding guide shaft play.

(3) As no sliding guide shaft is provided, the overall structure of the apparatus can be simple and inexpensive.

The cutting knife 18 may be mounted to the second end of the vertical pressure sensor 15 which is joined at the first end by a link 16 to one end of the parallel pressure sensor 17 which is fixedly mounted at the other end to the nut unit 14.

(Second Embodiment)

FIG. 3 is a front explanatory view of a coating adhesive strength and shear strength measuring apparatus according to a second embodiment of the present invention.

The coating adhesive strength and shear strength measuring apparatus denoted at 200 has a piezoelectric device driving slightly movable stage 30h fixedly mounted on a support base 1 thereof.

The piezoelectric device driving slightly movable stage 30h includes a stage 36h which is driven by a piezoelectric device to move in one direction relative to a frame 35h (e.g. the trade name "Nano-stage" of NANOCONROL Co.,Ltd).

The piezoelectric device driving slightly movable stage 30h is fixedly mounted at its frame 35h to the support base 1 so that its relative movement is carried out in a horizontal direction. This allows the stage 36h to move horizontally over the support base 1. The horizontal movement of the stage 36h may be within 300 μm.

A link rod 32 is fixedly mounted at the lower end to the stage 36h of the piezoelectric device driving slightly movable stage 30h.

The other end of the link rod 32 is joined to another piezoelectric device driving slightly movable stage 30v.

The piezoelectric device driving slightly movable stage 30v includes a stage 36v which is driven by a piezoelectric device to move in one direction relative to a frame 35v (e.g. the trade name "Nano-stage" of NANOCONROL Co.,Ltd).

The piezoelectric device driving slightly movable stage 30v is fixedly mounted at its stage 36v to the link rod 32 so that its relative movement is carried out in a vertical direction. This allows the frame 35v to move vertically over the support base 1. The vertical movement of the frame 35v may be within 100 μm.

A vertical pressure sensor 15 is fixedly mounted at one end to the frame 35v of the piezoelectric device driving slightly movable stage 30v.

The vertical pressure sensor 15 is a weighing load cell (e.g. CB17 of MINEBEA CO.,LTD) for measuring the pressure exerted in a vertical direction on the other end thereof.

The first end of a parallel pressure sensor 17 is fixedly mounted by a link 16 to the other end of the vertical pressure sensor 15.

The parallel pressure sensor 17 is a weighing load cell (e.g. CB17 of MINEBEA CO.,LTD) for measuring the pressure exerted in a horizontal direction on the second end thereof.

A cutting knife 18 is fixedly mounted to the second end of the parallel pressure sensor 17.

In addition, a vertical displacement sensor 19 is fixedly mounted by a support 20 to a cutting knife holder end of the parallel pressure sensor 17.

A test piece S is a coated strip which is held with its coating surface extending horizontally between a test piece bed 23 and a clamp 22.

The two piezoelectric device driving slightly movable stage 30h and 30v are connected by an output interface 38a (e.g. the trade name "Nano-servo controller" of NANOCONROL Co.,Ltd) to a personal computer 28.

The vertical pressure sensor 15, the parallel pressure sensor 17, and the vertical displacement sensor 19 are connected by an input interface 28b to the personal computer 28.

Upon receiving a command from the operator, the personal computer 28 actuates the two piezoelectric device driving slightly movable stages 30h and 30v to cut the coating of the test piece S. The personal computer 28 then receives a measurement of the vertical pressure from the vertical pressure sensor 15, a measurement of the parallel pressure from the parallel pressure sensor 17, and a depth of the cutting from the vertical displacement sensor 19. The vertical pressure, the parallel pressure, and the depth of the cutting are then converted into graphic representations which are displayed on a display or printed down by a printer.

The measurement of the coating adhesive strength and shear strength is conducted by the following steps.

(1) A test piece S is placed on the test piece bed 23 by the clamp 22 with its coating surface extending horizontally. The edge of the cutting knife 18 is set in parallel to the coating surface of the test piece S. In case of using a tiltable test piece head, the coating surface of the test piece S is set in parallel to the edge of the cutting knife 18.

(2) The cutting knife 18 is lifted down by the action of the piezoelectric device driving slightly movable stage 30v until it exerts a predetermined load (e.g. 1 g) against the coating surface of the test piece S. It is then determined that the depth of the cutting read from the vertical displacement sensor 19 is zero at the time.

(3) The cutting knife 18 is moved in both, horizontal and vertical, directions by the action of the two piezoelectric device driving slightly movable stages 30h and 30v so that its edge cuts into the coating of the test piece S as shown in FIG. 2. In case that the two pressure sensors 15 and 17 are forced and deformed by any pressure during the cutting operation, the cutting plane is constantly kept parallel by due to maintain the shape of parallelogram thus holding the cutting knife 18 at a desired cutting angle to the test piece S.

(4) The vertical pressure (a repulsion) is measured from the output of the vertical pressure sensor 15, the parallel pressure (a resistance to the cutting action) is measured from the output the parallel pressure sensor 17, and the depth of the cutting is measured from the output of the vertical displacement sensor 19. Th measurements of the changes in the vertical pressure, parallel pressure, and depth of the cutting are then examined.

The coating adhesive strength and shear strength measuring apparatus 200 of this embodiment employs the two piezoelectric device driving slightly movable stages 30h and 30v thus allowing its primary components from the support base 1 to the cutting knife 18 to be integrally assembled with no clearance as one unit whereby the measurement can highly be accurate.

(Other Embodiments)

(1) The cutting knife 18 may be replaced by a needle probe type sensor. This permits examination of the resistance to physical injury of the coating.

(2) The cutting knife 18 may be replaced by a flat tip probe type sensor. This permits examination of the frictional property such as friction coefficient.

As set forth above, each coating adhesive strength and shear strength measuring apparatus according to the present invention can measure both the adhesive strength and the shear strength of a coating at higher accuracy. Also, its structure can be built with ease and at less cost. Moreover, its overall weight can be minimized thus contributing to the portable design of the apparatus.

What is claimed is:

1. A coating adhesive strength and shear strength measuring apparatus for cutting a coating of a test piece with a cutting knife, measuring a force vertical to the coating and a force parallel to the coating which both are exerted on the cutting knife, and calculating adhesive strength and shear strength of the coating, comprising:

a stage arranged to be movable in vertical and parallel directions relative to the coating;

a vertical pressure sensor for measuring the vertical force exerted on the cutting knife, the vertical pressure sensor having a first end and a second end and being linked at the first end to the stage;

a parallel pressure sensor for measuring the parallel force exerted on the cutting knife, the parallel pressure sensor having a first end and a second end and being fixedly linked at the first end to the second end of the vertical pressure sensor such that the first end of the parallel pressure sensor is fixed relative to the second end of the vertical pressure sensor; and the cutting knife being linked to the second end of the parallel pressure sensor.

2. A coating adhesive strength and shear strength measuring apparatus for cutting a coating of a test piece with a cutting knife, measuring a force vertical to the coating and a force parallel to the coating which both are exerted on the cutting knife, and calculating adhesive strength and shear strength of the coating, comprising:

a stage arranged to be movable in vertical and parallel directions relative to the coating;

a parallel pressure sensor for measuring the parallel force exerted on the cutting knife, the parallel pressure sensor having a first end and a second end and being linked at the first end to the stage;

a vertical pressure sensor for measuring the vertical force exerted on the cutting knife, the vertical pressure sensor having a first end and a second end and being fixedly linked at the first end to the second end of the parallel pressure sensor such that the first end of the vertical pressure sensor is fixed relative to the second end of the parallel pressure sensor; and the cutting knife being linked to the second end of the vertical pressure sensor.

3. A coating adhesive strength and shear strength measuring apparatus according to claim 1 or 2, further comprising piezoelectric drives for moving the stage up to 500 µm.

4. A coating adhesive strength and shear strength measuring apparatus according to claim 1 or 2, further comprising:

graphic means for converting changes in the vertical pressure measured by the vertical pressure sensor, the parallel pressure measured by the parallel pressure sensor, and a depth of cutting by the cutting knife into graphic representations.

5. A coating adhesive strength and shear strength measuring apparatus according to claim 1, further comprising a link member directly connected to the first end of the parallel pressure sensor and to the second end of the vertical pressure sensor.

6. A coating adhesive strength and shear strength measuring apparatus according to claim 1, wherein the second end of the parallel pressure sensor is fixedly and directly connected to the cutting knife.

7. A coating adhesive strength and shear strength measuring apparatus according to claim 1, further comprising:

a support connected to the parallel pressure sensor; and a vertical displacement sensor fixedly mounted on the support for measuring a cutting depth of the cutting knife.

8. A coating adhesive strength and shear strength measuring apparatus according to claim 1, wherein there is no sliding guide shaft between the cutting knife and the parallel pressure sensor.

9. A coating adhesive strength and shear strength measuring apparatus according to claim 1, wherein there is no sliding guide shaft between the cutting knife and the vertical pressure sensor.

10. A coating adhesive strength and shear strength measuring apparatus according to claim 1, wherein the cutting knife is fixedly mounted to the second end of the parallel pressure sensor.

11. A coating adhesive strength and shear strength measuring apparatus according to claim 2, further comprising a link member directly connected to the first end of the vertical pressure sensor and to the second end of the parallel pressure sensor.

12. A coating adhesive strength and shear strength measuring apparatus according to claim 2, wherein the second end of the vertical pressure sensor is fixedly and directly connected to the cutting knife.

13. A coating adhesive strength and shear strength measuring apparatus according to claim 2, further comprising:

a support connected to the vertical pressure sensor; and a vertical displacement sensor fixedly mounted on the support for measuring a cutting depth of the cutting knife.

14. A coating adhesive strength and shear strength measuring apparatus according to claim 2, wherein there is no sliding guide shaft between the cutting knife and the parallel pressure sensor.

15. A coating adhesive strength and shear strength measuring apparatus according to claim 2, wherein there is no sliding guide shaft between the cutting knife and the vertical pressure sensor.

16. A coating adhesive strength and shear strength measuring apparatus according to claim 2, wherein the cutting knife is fixedly mounted to the second end of the vertical pressure sensor.

17. A coating adhesive strength and shear strength measuring apparatus, comprising:

a cutting knife for cutting a coating of a test piece such that a force vertical to the coating and a force parallel to the coating are exerted on the cutting knife;

a stage arranged to be movable in vertical and parallel directions relative to the coating;

a first pressure sensor for measuring the parallel or vertical force exerted on the cutting knife, the first pressure sensor having a first end and a second end and being linked at the first end to the stage; and a second pressure sensor for measuring the other of the parallel or vertical force exerted on the cutting knife, the second pressure sensor having a first end and a second end and being fixedly linked at the first end to the second end of the first pressure sensor such that the first end of the second pressure sensor is fixed relative to the second end of the first pressure sensor;

the cutting knife being fixedly mounted to the second end of the second pressure sensor.

18. A coating adhesive strength and shear strength measuring apparatus according to claim 17, wherein the first pressure sensor is arranged to measure the parallel force exerted on the cutting knife and the second pressure sensor is arranged to measure the vertical force exerted on the cutting knife.

* * * * *